US00PP13022P2

(12) United States Plant Patent
Utecht

(10) Patent No.: US PP13,022 P2
(45) Date of Patent: Oct. 1, 2002

(54) GERANIUM PLANT NAMED 'LULUMEX'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/657,549

(22) Filed: Sep. 8, 2000

(51) Int. Cl.[7] ..... A01H 5/00
(52) U.S. Cl. ..... Plt./332
(58) Field of Search ..... Plt./332, 324

(56) References Cited

FOREIGN PATENT DOCUMENTS

| | | |
|---|---|---|
| CA | 99-1631 | 4/1999 |
| DE | PEL 1461 | 6/1998 |
| EP | 99/0967 | 6/1999 |

OTHER PUBLICATIONS

1999/2000 Fischer Selections Catalogue featuring Lulumex.
Pelfi Fischer Peltatum '99 featuring 'Lulumex'.
GTITM UPOVROM Citation for 'Lulumex' as per CA PBR 99–1631; Apr. 14, 1999.*
GTITM UPOVROM Citation for 'Lulumex' as per QZ PBR 990967; Jun. 30, 1999.*
Licensing Agreement for 'Lulumex', 1999.*

* cited by examiner

*Primary Examiner*—Kent L. Bell
(74) *Attorney, Agent, or Firm*—Foley & Lardner

(57) ABSTRACT

Geranium 'Lulumex' is a new and distinct cultivar of geranium plant, particularly characterized by the combined features of bicolored, red-purple and white flower color, floriferous with large inflorescence, intense green foliage with distinct zonation, and moderately compact, well-branched and round plant habit.

1 Drawing Sheet

BACKGROUND OF THE INVENTION

The present invention comprises a new and distinct cultivar of geranium botanically known as *Pelargonium peltatum*, and hereinafter referred to by the cultivar name 'Lulumex'.

'Lulumex' is a product of a planned breeding program which had the objective of creating new ivy geranium varieties with variegated flowers with pink, red or purple main flower.

'Lulumex' originated from a grafting hybrid derived by grafting cuttings of 'Fislulu' on rootstocks of 'Mexicana' (Rouletta), in order to transmit the characteristic of variegation of flower color. The variegation causing agent is supposed to be a beneficial, virus-like organism.

'Fislulu' is a commercial ivy geranium variety, U.S. Plant Pat. No. 12,228, having deep purple double flowers, medium green, zoned foliage, and relatively compact, well-branched plant habit.

'Mexicana', synonym 'Rouletta', is an unpatented variety characterized by bicolored flowers with cherry-red bordered petals and white center, medium green foliage with zonation, and tall, open, long trailing plant habit.

Shoot tip cuttings of 'Fislulu' were grafted on branches of a potted plant of 'Mexicana' in a green-house in Hillscheid, Germany, in winter 1996/97 by the inventor Angelika Utecht. In April/May 1997 recently grown shoot tips from the successful graftings were cut, rooted and grown out.

Plants grown from cuttings of these plants were examined in Hillscheid in early spring 1998, and proved to develop variegated flowers only, which was confirmed during the common spring trial cultivation starting in May 1998.

In contrast to earlier experiments with grafting, the degree of variegation proved to be very uniform and the size of the white area of the petal was only temporarily reduced after the plants had grown rapidly under high temperature and high light intensity in spring.

Horticultural examination of plants grown from cuttings of the clone initiated in spring 1998 in Hillscheid, Federal Republic of Germany, and continuing thereafter, has demonstrated that the combination of characteristics as herein disclosed for 'Lulumex' are firmly fixed and are retained through successive generations of asexual reproduction.

BRIEF DESCRIPTION OF THE DRAWINGS

The accompanying photographic drawing shows typical flower and foliage characteristics of 'Lulumex' with colors being as true as possible with illustrations of this type.

In the following description color references are made to The Royal Horticultural Society Colour Chart. The color values were determined indoors from plants developed in a greenhouse in May 1999 in Hillscheid, Germany.

BRIEF DESCRIPTION OF THE NEW VARIETY

The following traits have been repeatedly observed and are determined to be basic charactertics of 'Lulumex', which in combination distinguish this geranium as a new and distinct cultivar:

1. Brilliant red-purple main flower color, and petals with a white center;
2. Semi-spherically shaped, relatively large inflorescence;
3. Medium green foliage with weak zonation;
4. Short to medium sized plant habit, very well-branched, round plant habit; and
5. Early to medium flowering response.

Of the many commercial cultivars known to the present inventor, the most similar in comparison to 'Lulumex' are the related varieties 'Fislulu' and 'Mexicana'.

In comparison to 'Fislulu', 'Lulumex' has variegated flowers with large white 'eyes' on petals and with a slightly different, brighter main flower color, that is, color of the margin of the petal. The morphological characteristics of 'Lulumex' are fairly close to those of 'Fislulu', apart from the even more freely branching.

In comparison to 'Mexicana', 'Lulumex' has a more intense main flower color, rounder florets, much more compact plant habit, and a distinctly higher number of branches.

'Lulumex' has not been observed under all possible environmental conditions. The phenotype may vary significantly with variations in environment such as temperature, light intensity and day length.

DETAILED BOTANICAL DESCRIPTION

The following observations, measurements, and comparisons describe 12 week old plants grown in Hillscheid, Germany, and in Langley, Bristish Columbia, Canada, under greenhouse conditions which approximate those generally used in commercial practice.

The measurements were taken in Langley, Canada, on Jun. 15, 1999,—12 weeks after planting of rooted cuttings into 15 cm pots.

CLASSIFICATION

Botanical: A hybrid of the species *Pelargonium peltatum* L'Hérit.

Commercial: *Ivy geranium*, cv. LULUMEX.

INFLORESCENCE

Umbel:

*Shape.*—Nearly semi-spherical.

*Average diameter.*—87 mm.

*Average depth.*—45 mm.

*Peduncle length.*—105 mm.

*Peduncle color.*—Light green, varying between RHS 143 B and RHS 144 A.

*Pedicel length.*—28.5 mm, with spur.

*Pedicel color.*—Yellowish green, RHS 144 A, occasionally slight infusion of anthocyanin, weak brownish, RHS 179 B.

*Number of flowers per umbel.*—6–9.

Corolla:

*Average diameter.*—52 mm.

*Form.*—Double.

*Shape.*—Round outline, but slightly zygomorph.

*Number of petals.*—16.5.

*Shape of upper petals.*—Narrow obovate, attenuate base, upper end rounded, margin entire.

*Shape of lower petals.*—Obovate, attenuate base, upper end rounded, margin entire.

*Size of upper petals.*—30–32 mm in length, 19–21 mm in width.

*Size of lower petals.*—28–30 mm in length, 21–23 mm in width.

*Number of petaloids.*—2–4.

*Shape of petaloids.*—Filiform to narow-lanceolate.

*Size of petaloids.*—Approximately 9–11 mm long, more narrow than the petals.

*Color of petaloids.*—Approximately RHS 74 B, with white base, RHS 155 D (Both surfaces).

*Color (general tonality from a distance of three meters)* .—Bicolored, brilliant red-purple and white.

*Color of upper petals (margin)*—From RHS 66 A to RHS 74 B.

*Markings of upper petals.*—Weak, two violet veins at the base, RHS 187 B.

*Color of lower petals (margin).*—From RHS 66 A to RHS 74 B.

*Color of middle of petals.*—White, RHS 155 D on both upper and lower.

*Color of lower surface of petals.*—Purple RHS 74 B at the margin, and white RHS 155 D in the middle.

*Color of sepals.*—Green, RHS 143 C on the upper side, and RHS 143 B on the under side.

*Number of sepals.*—5–6.

*Shape of sepals.*—Linear to lanceolate, acute apex.

*Size of sepals.*—12–13 mm long, largest sepal 4–5 mm wide, other sepals 3 mm wide.

Bud: (just before petals unfold):

*Shape.*—Narrow elliptical.

*Color (sepals).*—Medium green, from RHS 143 A to RHS 143 B.

*Color (petals).*—Mainly red, RHS 57 B, and white, RHS 155 D.

*Length.*—22 mm.

*Width.*—11 mm.

Reproductive organs:

*Androecium.*—Most often 5 fertile anthers, mainly white, with upper end pink, filaments, yellow-orange pollen, the lower side of mature anthers is black.

*Gynoecium.*—5–6-lobed stigma, violet stigma and whitish filament, one pistil per flower.

*Fertility/seed set.*—Hardly any spontaneous seed set.

Spring flowering response period: In Hillscheid, Germany, in 1999 plants had on average 1.0 flowers opened 12 weeks after planting of rooted cuttings (pinched plants).

Outdoor flower production: Relatively floriferous.

Durability: Fair shatter resistance. Good rain resistance. Good stability of flower color.

Lastingness of the individual bloom: Approximately 8 to 9 days at about 18° C.

Fragrance: None.

PLANT

Foliage:

*Form.*—Kidney-shaped with weak, rounded lobes, reniform, closed to slightly overlapping base, and with glossy surface.

*Margin.*—Entire.

*Size of leaf.*—83 mm in width, average 48 mm in length.

*Color of upper surface.*—Medium green, approx. RHS 137 B.

*Color of lower surface.*—RHS 137 D.

*Color of zonation.*—Weak to medium distinct, brown, about RHS 166 A.

*Size of petioles.*—40–50 mm in length, 2–3 mm in diameter.

*Color of petioles.*—Light green, RHS 143 C.

*Disease/pest resistance/susceptibility.*—No specific observations made other than typical for ivy cultivars: due to thick, leathery and glossy surface of the leaves, they are generally not susceptible to diseases however not completely resistant to aphids: tolerance to botrytis is relatively good.

General appearance and form:

*Internode length.*—25–35 mm.

*Branching pattern.*—11.9 branches.

*Plant size.*—16.3 cm from soil level to top of the foliage canopy (12 weeks after planting); 60 cm from base of the main stem to the tips of the stems, 30–32 cm in diameter (30 weeks after planting).

I claim:

1. A new and distinct cultivar of Geranium plant 'Lulumex', as described and illustrated.

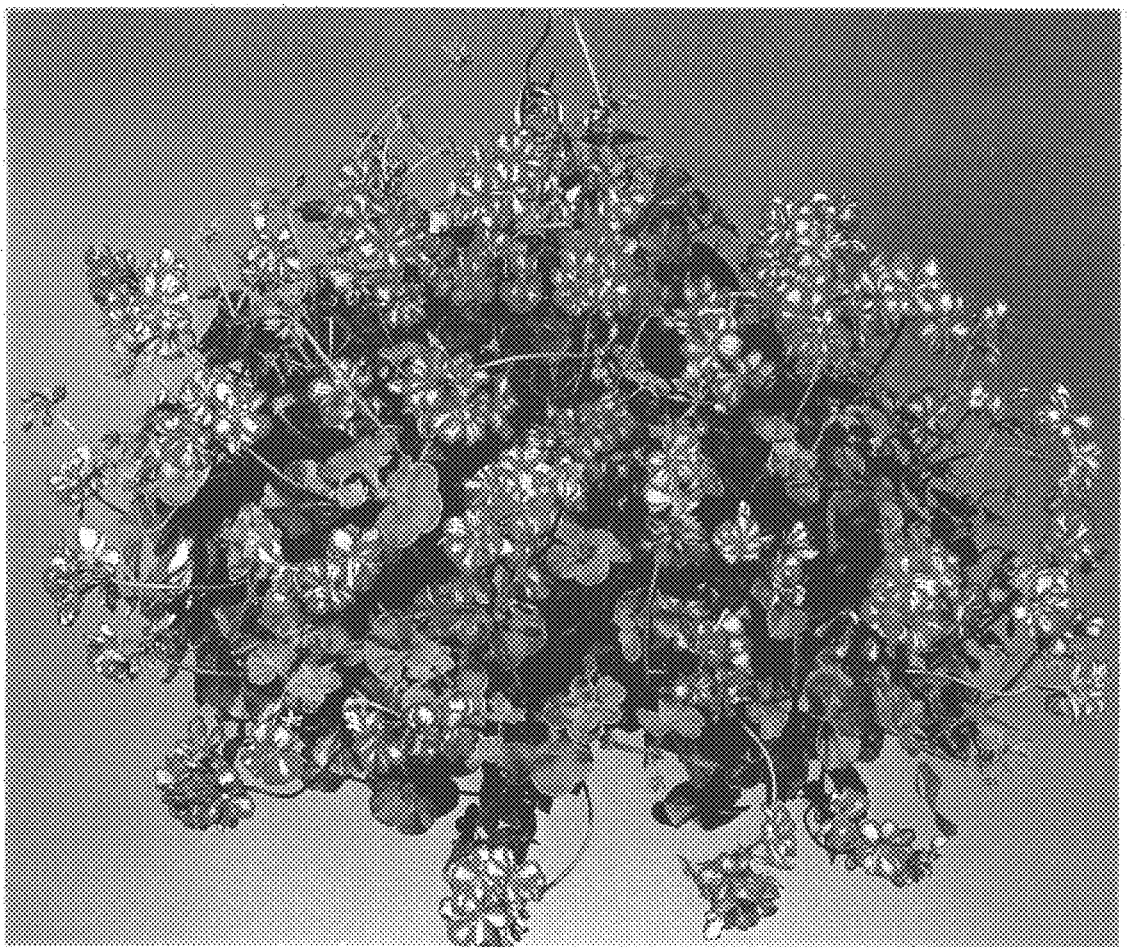

* * * * *